(12) United States Patent
Monden

(10) Patent No.: US 11,734,951 B2
(45) Date of Patent: *Aug. 22, 2023

(54) FAKE-FINGER DETERMINATION DEVICE, FAKE-FINGER DETERMINATION METHOD, AND FAKE-FINGER DETERMINATION PROGRAM

(71) Applicant: NEC Corporation, Tokyo (JP)

(72) Inventor: Akira Monden, Tokyo (JP)

(73) Assignee: NEC CORPORATION, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 17/881,675

(22) Filed: Aug. 5, 2022

(65) Prior Publication Data

US 2022/0369956 A1 Nov. 24, 2022

Related U.S. Application Data

(63) Continuation of application No. 16/679,557, filed on Nov. 11, 2019, now Pat. No. 11,443,548, which is a
(Continued)

(30) Foreign Application Priority Data

Nov. 10, 2009 (JP) ................. 2009-256971

(51) Int. Cl.
*G06V 40/12* (2022.01)
*G06V 10/26* (2022.01)
(Continued)

(52) U.S. Cl.
CPC ........ *G06V 40/1388* (2022.01); *A61B 5/1172* (2013.01); *G06V 10/26* (2022.01);
(Continued)

(58) Field of Classification Search
CPC .... G06K 9/00114; G06K 9/4652; G06K 9/34; G06K 2009/0006
See application file for complete search history.

(56) References Cited

U.S. PATENT DOCUMENTS 5,937,082 A 8/1999 Funada
6,118,891 A 9/2000 Funada
(Continued)

FOREIGN PATENT DOCUMENTS

CN 101226589 A 7/2008
JP 2637253 B2 3/1997
(Continued)

OTHER PUBLICATIONS

Communication dated Jul. 21, 2017, from the European Patent Office in counterpart European application No. 10829796.1.
(Continued)

*Primary Examiner* — On S Mung

(57) ABSTRACT

A fake finger in which a transparent thin film is attached to a finger surface is discriminated. A fake-finger determination device includes: an imaging unit 10 that captures an authentication object as a fingerprint authentication object; a classifying unit 31 that classifies an image captured by the imaging unit 10 into a plurality of regions including at least a skin region and a background region using colors of pixels included in the image; and a determining unit 32 that determines whether or not a foreign substance is present in the periphery of a finger based on a feature of a region classified as neither the skin region nor the background region out of the regions classified by the classifying unit 31.

7 Claims, 4 Drawing Sheets

Related U.S. Application Data continuation of application No. 13/508,682, filed as application No. PCT/JP2010/067551 on Oct. 6, 2010, now Pat. No. 10,496,871.

(51) Int. Cl.
  *G06V 10/56* (2022.01)
  *A61B 5/1172* (2016.01)

(52) U.S. Cl.
  CPC .......... *G06V 10/56* (2022.01); *G06V 40/1347* (2022.01); *G06V 40/1382* (2022.01); *G06V 40/1341* (2022.01)

(56) References Cited

U.S. PATENT DOCUMENTS

| | | |
|---|---|---|
| 6,560,352 B2 | 5/2003 | Rowe et al. |
| 10,296,871 B2 | 5/2019 | Mo et al. |
| 2003/0025897 A1 | 2/2003 | Iwai |
| 2005/0271258 A1 | 12/2005 | Rowe |
| 2006/0147096 A1 | 7/2006 | Lee et al. |
| 2007/0014443 A1 | 1/2007 | Russo |
| 2007/0036400 A1 | 2/2007 | Watanabe et al. |
| 2009/0232367 A1 | 9/2009 | Shinzaki |
| 2009/0304237 A1 | 12/2009 | Yoshikawa et al. |

FOREIGN PATENT DOCUMENTS

| | | |
|---|---|---|
| JP | 09-167230 A | 6/1997 |
| JP | 2002-177624 A | 6/2002 |
| JP | 2003-006645 A | 1/2003 |
| JP | 2003-050993 A | 2/2003 |
| WO | 03002013 A1 | 1/2003 |
| WO | 2006-277415 A | 10/2006 |

OTHER PUBLICATIONS

State Intellectual Property Office of P. R. China, Office Action dated May 28, 20214 issued in a corresponding Chinese Application No. 201080051084.1.

Lee, K., et al., "A Study on Multi-unit Fingerprint Verification", 2005, Audio- and Video-Based Biometric Person Authentication, Springer-Verlag, Berlin/Heidelberg. pp. 141-150 (10 pages).

European Communication dated May 15, 2017 issued in EP Application 10829796.1.

Madisetti, V., et al., "Digital Signal Processing Handbook", Digital Signal Processing Handbook, 1999, CRC Press. 51.10.3. pp. 1125-1127 (4 pages).

Office Communication for CN Application No. 201080061084.1, dated Mar. 28, 2014.

FAKE-FINGER DETERMINATION DEVICE, FAKE-FINGER DETERMINATION METHOD, AND FAKE-FINGER DETERMINATION PROGRAM

CROSS-REFERENCE TO RELATED APPLICATIONS

The present application is a continuation application of U.S. patent application Ser. No. 16/679,557 filed on Nov. 11, 2019, which is a continuation application of U.S. patent application Ser. No. 13/508,682 filed on May 8, 2012, which is issued as U.S. Pat. No. 10,496,871, which is a National Stage Entry of international application PCT/JP2010/067551 filed on Oct. 6, 2010, which claims the benefit of priority from Japanese Patent Application No. 2009-256971 filed on Nov. 10, 2009, the disclosures of all of which are incorporated in their entirety by reference herein.

The present invention relates to a fake-finger determination device, a fake-finger determination method, and a fake-finger determination program.

BACKGROUND

In recent years, fingerprint authentication has been attracting attention as one of authentication methods for identifying an individual. Fingerprints differ person to person and have a feature that does not change even though years have passed.

Thus, fingerprint authentication is considered having higher reliability than currently prevailing password authentication and the like. Meanwhile, in fingerprint authentication, it is necessary to prevent wrongdoing that someone impersonates another person using a fake finger forged using another person's fingerprint. As techniques for preventing such wrongdoing, for example, Patent Documents 1 and 2 disclose techniques of detecting a fake finger based on a color of a surface of a finger irradiated with light.

Patent Document 1: Patent Publication JP-A-2003-50993
Patent Document 2: Japanese Patent Publication No. 2637253

However, in Patent Documents 1 and 2, since a fake finger is detected based on a color of a surface of a finger, a fake finger made such that a transparent or flesh-colored thin film duplicated from another person's fingerprint is attached to a surface of a finger is hardly discriminated. This is because, in Patent Documents 1 and 2, a fake finger with a transparent thin film attached thereto is hardly discriminated since a color of a fake finger surface assimilates with a color of a skin.

SUMMARY

The invention has been made to solve the above-mentioned problems, and it is an object of the present invention to provide a fake-finger determination device, a fake-finger determination method, and a fake-finger determination program, which are capable of determining a fake finger in which the transparent thin film is attached to the surface of the finger.

According to an aspect of the invention, there is provided a fake-finger determination device including: an imaging unit that captures an authentication object as a fingerprint authentication object; a classifying unit that classifies an image captured by the imaging unit into a plurality of regions including at least a skin region and a background region using colors of pixels included in the image; and a determining unit that determines whether or not a foreign substance is present in the periphery of a finger based on a feature of a region classified as neither the skin region nor the background region out of the regions classified by the classifying unit.

According another aspect of the invention, there is provided a method of determining a fake finger, including the steps of: capturing an authentication object as a fingerprint authentication object; classifying an image captured in the capturing step into a plurality of regions including at least a skin region and a background region using colors of pixels included in the image; and determining whether or not a foreign substance is present in the periphery of a finger based on a feature of a region classified as neither the skin region nor the background region out of the regions classified in the classifying step.

A fake-finger determination program according to the present invention causes a computer to execute the steps included in the above method of determining the fake finger.

According to the invention, it is possible to determine a fake finger in which a transparent thin film is attached to a surface of a finger.

DETAILED DESCRIPTION

Hereinafter, exemplary embodiments of a fake-finger determination device, a fake-finger determination method, and a fake-finger determination program according to the present invention will be described.

First, how the inventors achieve the invention will be described. If a person who desires to impersonate another person using a transparent thin film forged from another person's fingerprint at the time of fingerprint authentication, the person needs to cover his/her fingerprint with the thin film. In this case, the size of the thin film is inevitably larger than a range in which a fingerprint of a finger is scanned. Therefore, a part of the thin film is considered to protrude in the periphery of the finger when the thin film is attached to the finger and then the fingerprint authentication is performed. The invention has been made by focusing on this problem and is characterized in that the fake finger in which a transparent thin film is attached to a finger surface is determined by detecting the thin film protruding in the periphery of the finger. Hereinafter, embodiments of the fake-finger determination device according to the invention will be described in detail on this premise.

First Embodiment

Figure 1:
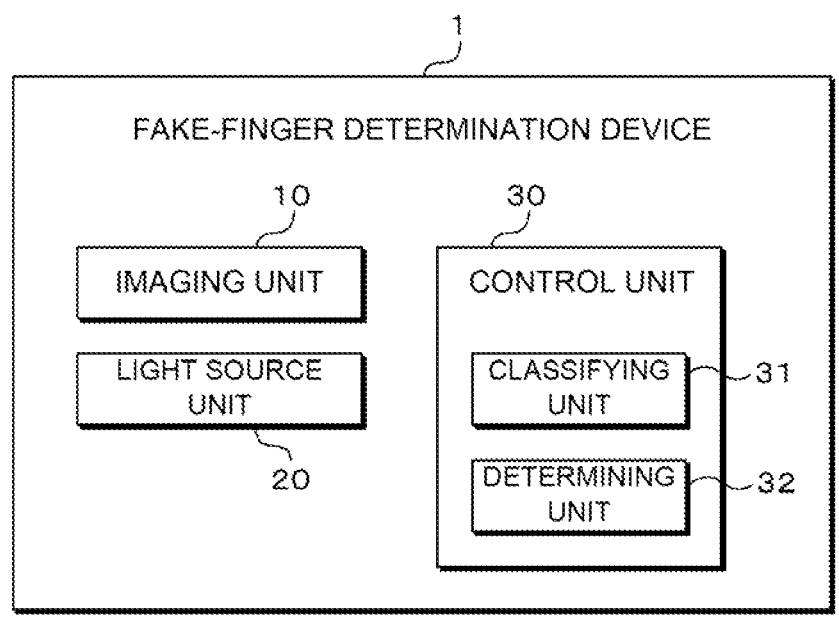
FIG. 1 is a block diagram illustrating a schematic configuration of a fake-finger determination device according to each embodiment.

First, a schematic configuration of a fake-finger determination device according to a first embodiment will be described with reference to FIG. 1. FIG. 1 is a diagram illustrating a schematic configuration of a fake-finger determination device according to each embodiment. A fake-finger determination device 1 is a device that determines whether or not an authentication object which is a fingerprint authentication object is a fake finger. For example, a finger that is an authentication object is placed on a predetermined placement area provided on a top surface of the fake-finger determination device 1.

As illustrated in FIG. 1, the fake-finger determination device 1 includes an imaging unit 10, a light source unit 20, and a control unit 30. The imaging unit 10 is, for example, a camera and captures an authentication object placed in the installation region. The light source unit 20 is, for example, a light-emitting diode (LED) and irradiates the authentication object with light when the imaging unit 10 captures the authentication object.

The imaging unit 10, the light source unit 20, and the control unit 30 of the fake-finger determination device 1 are similar to an imaging unit, a light source unit, and a control unit of a conventional fingerprint authentication device, respectively, in principle. However, the fingerprint authentication device of the invention is different from the conventional fingerprint authentication device in that the control unit 30 has various functions for determine whether or not an authentication object is authentic.

The fake-finger determination device 1 is physically configured to include a central processing unit (CPU), a memory, an imaging unit, and a light source unit. For example, the memory includes a read only memory (ROM) that stores a program or data processed by the CPU and a random access memory (RAM) used as various work areas mainly for control processing. The components are connected to one another via a bus. The CPU executes the program stored in the ROM and performs processing using data captured by the imaging unit or data developed in the RAM, so that function of the respective units of the fake-finger determination device 1, which will be described later, can be implemented.

The control unit 30 controls the fake-finger determination device 1 in general by executing a variety of control processes. For example, the control unit 30 includes a classifying unit 31 and a determining unit 32.

The classifying unit 31 classifies an image captured by the imaging unit 10 into a skin region, a background region, and a remaining region using colors of pixels included in the image. Specifically, the classifying unit 31 classifies the image into the skin region, the background region, and the remaining region in the following manner.

The classifying unit 31 divides the captured image into three regions by using a color of a pixel included in the image captured by the imaging unit 10 as a feature quantity. The feature quantity used to divide the image may include, for example, a hue value of a pixel. A technique of dividing the image into three regions may include, for example, a k-means technique.

The classifying unit 31 computes each representative value of each divided region. The representative value may include, for example, an average of the hue values of pixels included in each region, a hue value of a pixel most abundant in each region, or the like. The classifying unit 31 classifies a region having a representative value closest to a skin color as the skin region based on the representative value computed for each region. Whether or not the representative value is close to the skin color may be determined, for example, based on the hue value. Specifically, the classifying unit 31 sets a region having a hue value, as a representative value, within a predetermined range that can be treated as a skin color to the skin region out of three regions. The predetermined range may include, for example, a range of approximately 10 degrees to 50 degrees that can be treated as a flesh color corresponding to a skin color assuming that a red color is set to 0 degree in a hue, saturation, and value (HSV) color space. In addition, if there are a plurality of regions serving as a target of the skin region, for example, a region having a representative value closest to a center value of the predetermined range that can be treated as a skin color may be classified as the skin region.

The classifying unit 31 classifies a region having the representative value closer to the background color as the background region based on the representative values of two regions other than the skin region. Specifically, the classifying unit 31 sets a region having a hue value, as the representative value, within a predetermined range that can be treated as a background color out of two regions other than the skin region to the background region. In addition, in a case where both the representative values of two regions are within a predetermined range, for example, a region having a representative value closer to the center value of a predetermined range that can be treated as a background color can be classified as the background region. As a result, a region classified as neither the skin region nor the background region is classified as the remaining region. In addition, since white turbidity or the like may occur even when transparency of the thin film attached to the surface of the finger is high, a difference is inevitably generated between the background color and the color of the thin film. This allows to distinguish between the background region and the thin film region.

Figure 2:
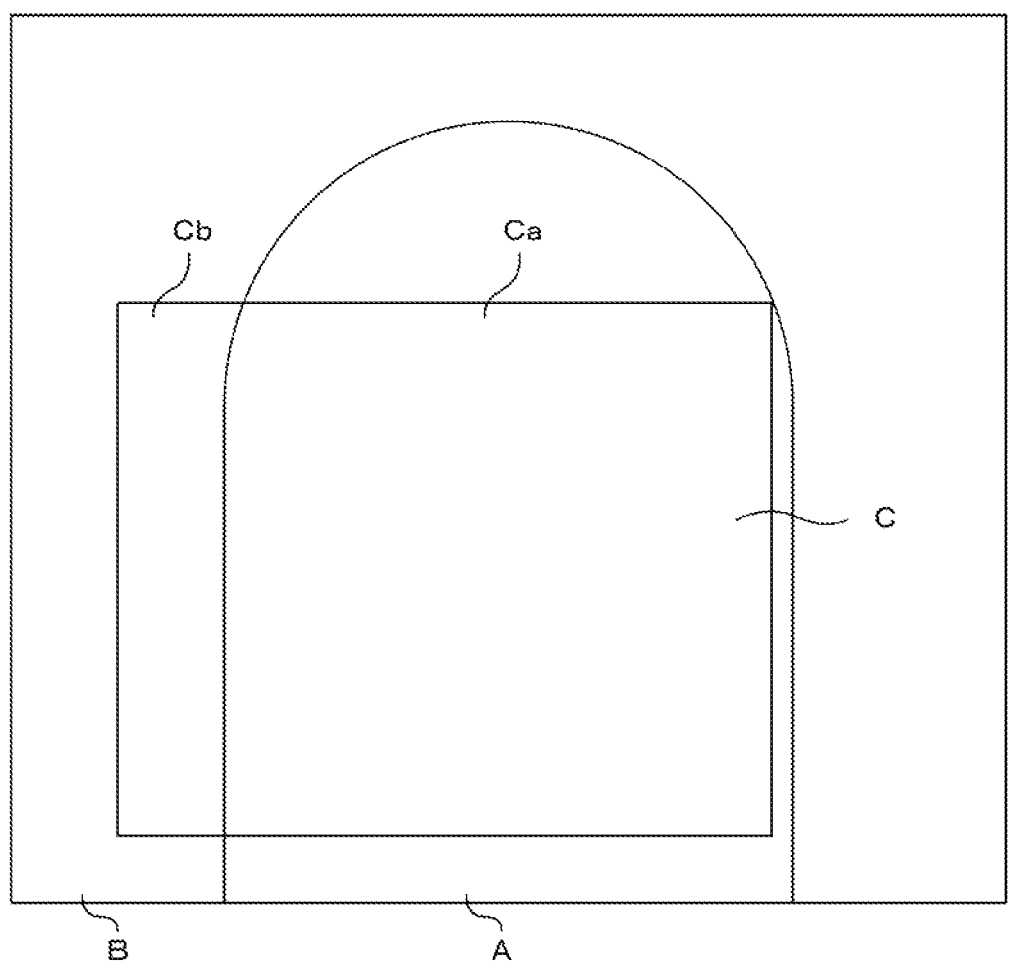
FIG. 2 is a schematic diagram illustrating a classifying state when a fake finger in which a transparent thin film is attached to a surface of a human finger is captured as an authentication object.

Here, detailed examples of the skin region, the background region, and the remaining region classified by the classifying unit 31 are illustrated in FIG. 2. FIG. 2 is a diagram schematically illustrating a classification state when the fake finger in which the transparent thin film is attached to the surface of the human finger as an authentication object is captured. The image A of FIG. 2 corresponds to a human finger, the image B corresponds to a background, and the image C corresponds to a transparent thin film. The classifying unit 31 divides the captured image into regions A and Ca, B, and Cb by using the colors of the pixels included in the captured image of FIG. 2 as the feature quantity. The classifying unit 31 classifies the regions A and Ca having the representative value closest to the skin color as the skin region based on the representative values of each divided region. The classifying unit 31 classifies the region B having the representative value closer to background color as the background region. The classifying unit 31 classifies the region Cb as the remaining region.

In addition, if the background color is not apparent, and it is difficult to set in advance, the range of the hue value that can be treated as the background color, the classification may be made by considering a positional relation between two regions other than the skin region. Specifically, the region located further outside of the skin region may be set as the background region. In addition, even when it is easy to set in advance, the range of the hue value that can be treated as the background color, the classification may be made by considering both the method of using the representative value and the method of using the positional relation.

The determining unit 32 determines whether or not the remaining region classified as neither the skin region nor the background region out of the regions classified by the classifying unit 31 is the region obtained by excessively dividing either the skin region or the background region. Whether or not the region is excessively divided may be determined, for example, based on a distance or similarity between the representative value of the remaining region and each representative value of the skin region or the background region.

If it is determined that the remaining region is the excessively divided region, it is determined that a foreign substance is not present in the periphery of the finger, that is, the authentication object is a human finger. In this manner, it is determined whether or not the remaining region is the excessively divided region, and it is determined that the authentication object is a human finger if the remaining region is the excessively divided region. Therefore, it is possible to prevent a case where a genuine human finger is erroneously determined as the fake finger when the fair human finger is placed.

The determining unit 32 determines whether or not a foreign substance is present in the periphery of the finger based on the size of the remaining region if it is determined that the remaining region is not the excessively divided region. Specifically, the determining unit 32 determines that a foreign substance is present in the periphery of the finger, that is, the authentication object is the fake finger, if the number of pixels of the remaining region is equal to or greater than a predetermined number. The predetermined number corresponds to, for example, an upper limit of the number of pixels (upper limit pixel number) detected as a noise.

Figure 3:
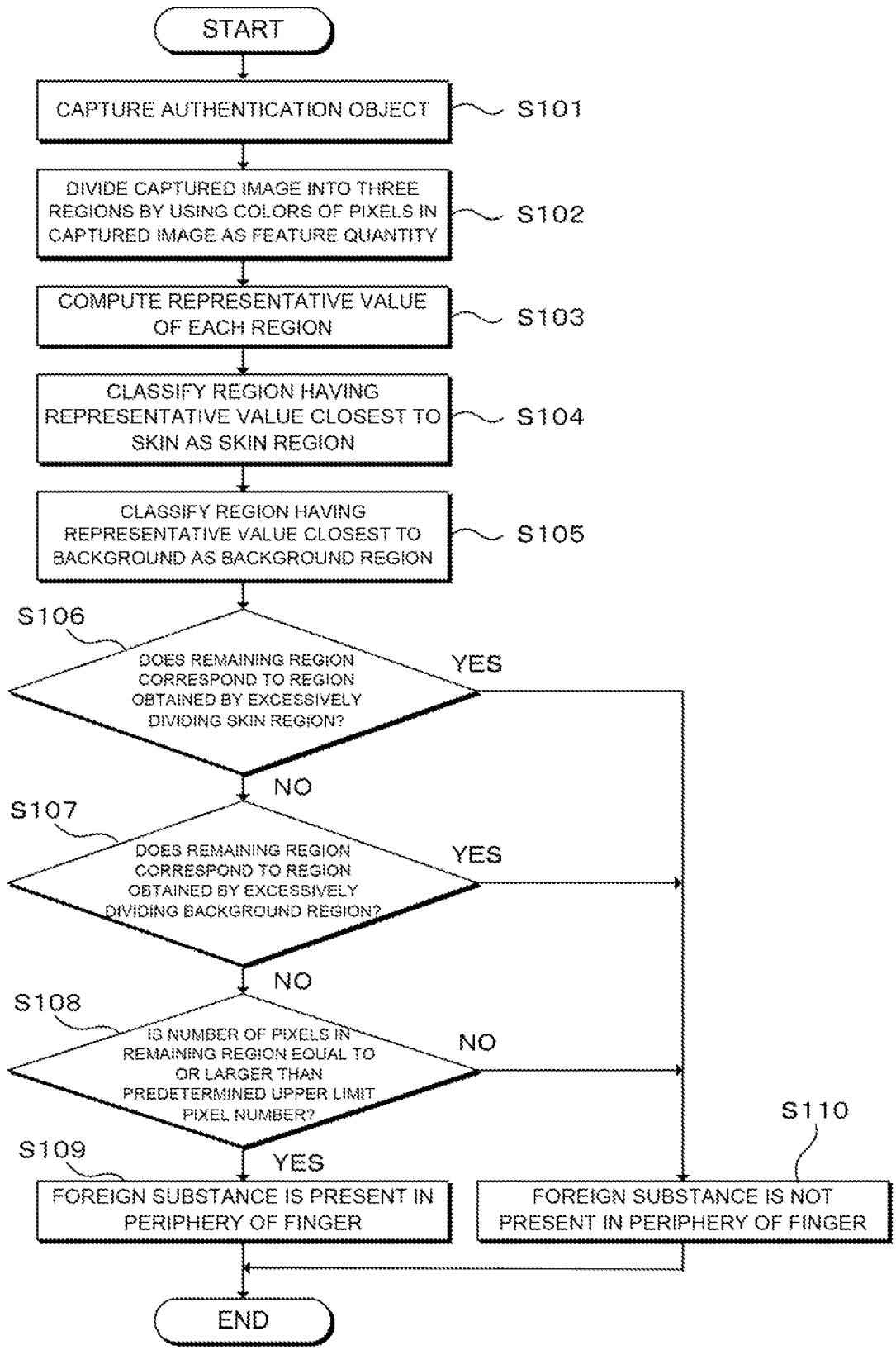
FIG. 3 is a flowchart illustrating a process procedure for determining a fake finger according to a first embodiment of the invention.

Next, a fake-finger determination process executed by the fake-finger determination device according to the first embodiment will be described with reference to FIG. 3. FIG. 3 is a flowchart illustrating a process procedure for determining a fake finger in which a transparent thin film is attached to a surface of a finger.

Initially, as the authentication object is placed in the installation region of the fake-finger determination device 1, the light source unit 20 irradiates light onto the authentication object, and the imaging unit 10 captures the authentication object (step S101).

Subsequently, the classifying unit 31 divides the image captured by the imaging unit 10 into three regions by using the colors of pixels included in the captured image as a feature quantity (step S102).

Subsequently, the classifying unit 31 computes each representative value of each region divided in step S102 described above (step S103).

Subsequently, the classifying unit 31 classifies the region having a representative value closest to a skin as the skin region based on the representative values of each region computed in step S103 described above (step S104).

Subsequently, the classifying unit 31 classifies a region having a representative value closest to the background as the background region based on the representative values of two regions other than the skin region (step S105).

Subsequently, the determining unit 32 determines whether or not the remaining region classified as neither the skin region nor the background region out of three regions divided in step S102 described above is a region obtained by excessively dividing the skin region (step S106). If it is determined YES in step S106, the process advances to step S110 described below.

Otherwise, if it is determined that the remaining region is not the region obtained by excessively dividing the skin region in step S106 described above (NO in step S106), the determining unit 32 determines whether or not the remaining region out of three regions divided in step S102 described above is the region obtained by excessively dividing the background region (step S107). If it is determined YES in step S107, the process advances to step S110 described below.

Otherwise, if it is determined that the representative value does not correspond to the region obtained by excessively dividing the background region in step S107 described above (NO in step S107), the determining unit 32 determines whether or not the number of pixels of the remaining region out of three regions divided in step S102 described above is equal to or greater than a predetermined upper limit pixel number (step S108). If it is determined NO in step S108, the determining unit 32 determines that a foreign substance is not present in the periphery of a finger (step S110). That is, it is determined that the authentication object is a human finger, and the fake-finger determining process is terminated.

Otherwise, if it is determined the number of pixels in the remaining region is equal to or greater than a predetermined upper limit pixel number in step S108 (YES in step S108), the determining unit 32 determines that a foreign substance is present in the periphery of a finger (step S109). That is, it is determined that the authentication object is the fake finger, and the fake-finger determining process is terminated.

As described above, in the fake-finger determination device 1 according to the first embodiment, the image captured by the imaging unit 10 can be classified into the skin region, the background region, and the remaining region. In addition, if the number of pixels in the remaining region is equal to or greater than a predetermined number, it can be determined that a foreign substance is present in the periphery of a finger. As a result, it is possible to detect the thin film portion protruding in the periphery of a finger even when the fake finger in which the transparent thin film is attached to the surface of the finger is used. Therefore, it is possible to improve determination accuracy of the fake finger.

In the fake-finger determination device 1 according to the first embodiment, it is determined whether or not the remaining region is the region obtained by excessively dividing the skin region or the background region. If it is determined that the remaining region is the excessively divided region, it is possible to determine that the fingerprint corresponds to a human finger. As a result, it is possible to prevent a case where a genuine human finger is erroneously determined as the fake finger when the fair human finger is placed.

Second Embodiment

The second embodiment of the invention will be described. A fake-finger determination device according to the second embodiment is different from the fake-finger determination device according to the first embodiment described above in the function of a classifying unit 31 of a control unit 30. Other configurations are similar to those of the fake-finger determination device according to the first embodiment. Therefore, like reference numerals denote like elements, and description thereof will not be repeated. The following description will focus on a difference between the first and second embodiments.

The classifying unit 31 according to the second embodiment is similar to the classifying unit 31 according to the first embodiment in that the image captured by an imaging unit 10 is classified into the skin region, the background region, and the remaining region using the colors of the pixels included in this image. However, a specific method of classifying the image into the skin region, the background region, and the remaining region is different. Hereinafter, how the classifying unit 31 classifies the image into the skin region, the background region, and the remaining region according to the second embodiment will be described in detail.

The classifying unit 31 classifies, as the skin region, a group of pixels having a color that can be treated as a skin out of each pixel included in the image captured by the imaging unit 10. The color that can be treated as a skin may include, for example, a hue value that can be treated as a skin. The hue value that can be treated as a skin corresponds to approximately 10 degrees to 50 degrees that can be treated as a hue value of a skin color assuming the hue value of a red color is set to 0 degree in the HSV color space.

The classifying unit 31 classifies, as the background region, a group of pixels having a color that can be treated as the background out of each pixel included in the image captured by the imaging unit 10. The color that can be treated as the background may include, for example, a hue value that can be treated as the background. As a result, a group of pixels classified as neither the skin region nor the background region are classified as the remaining region.

If the background color is not apparent, a portion corresponding to the skin region out of the image captured by the imaging unit 10 is divided into two regions by using the colors of pixels included in this portion as the feature quantity, and the region located in an outer side can be classified as the background region based on the positional relation between two divided regions. The feature quantity used in the dividing may include, for example, a hue value of the pixel. The method of dividing the image into two regions may include, for example, a k-means technique.

Figure 4:
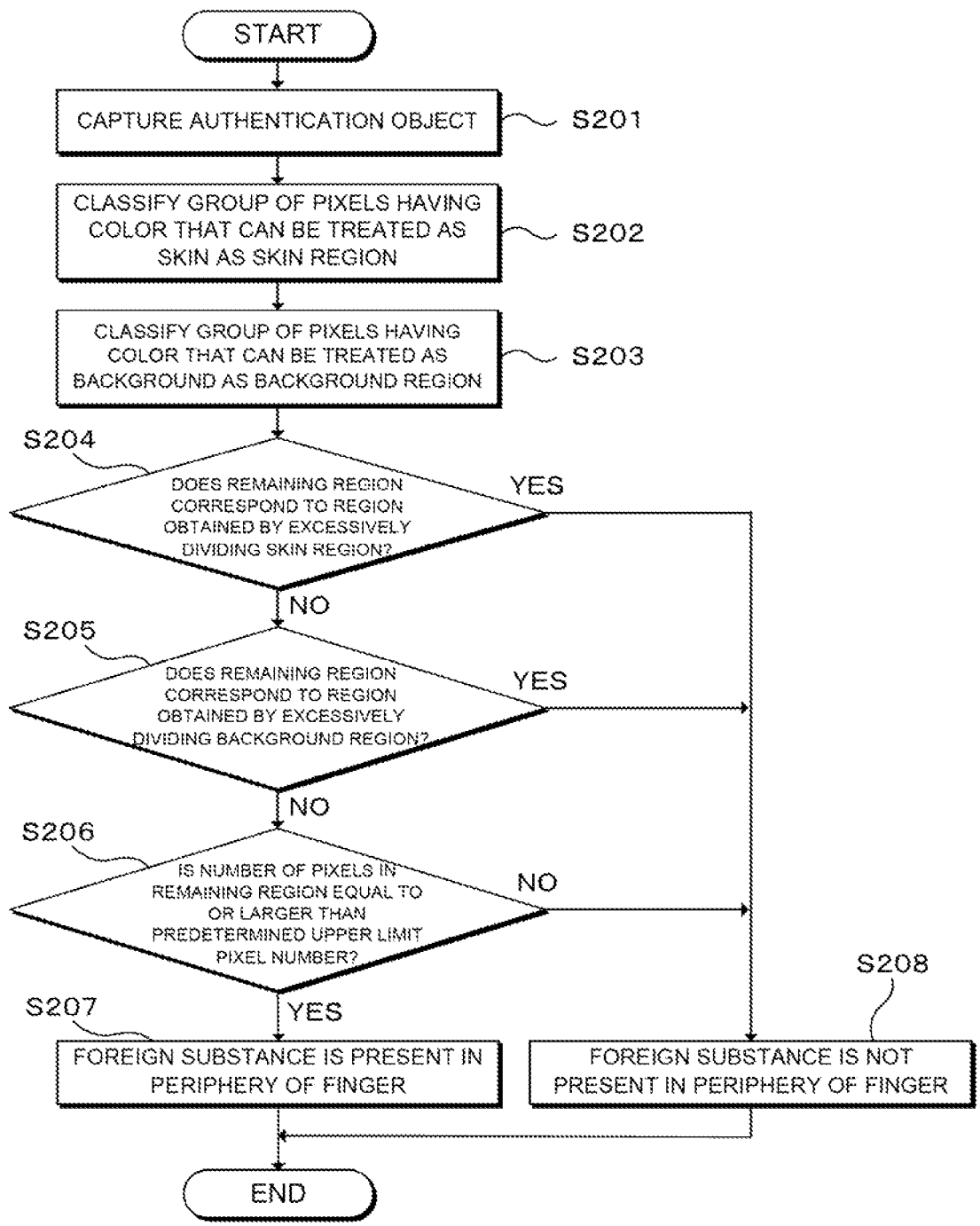
FIG. 4 is a flowchart illustrating a process procedure for determining a fake finger according to a second embodiment of the invention.

Next, a fake-finger determining process executed by the fake-finger determination device according to the second embodiment will be described with reference to FIG. 4. FIG. 4 is a flowchart illustrating a process procedure for determining the fake finger in which a transparent thin film is attached to the finger surface. Since steps S201 and S204 to S208 illustrated in FIG. 4 are similar to steps S101 and S106 to S110 of FIG. 3, they will not be repeatedly described. Here, the following description will focus on the processing details of steps S202 and S203 different from those of FIG. 3.

As shown in FIG. 4, when the authentication object is captured in step S201, the classifying unit 31 classifies, as the skin region, a group of pixels having a color that can be treated as a skin out of each pixel included in the image captured by the imaging unit 10 (step S202).

Subsequently, the classifying unit 31 classifies, as the background region, a group of pixels having a color that can be treated as a background out of each pixel included in the image captured by the imaging unit 10 (step S203).

Then, similar to the first embodiment described above, the determining unit 32 determines whether or not the remaining region classified as neither the skin region nor the background region is the region obtained by excessively dividing the skin region or the background region (steps S204 and S205) and whether or not the number of pixels in the remaining region is equal to or greater than a predetermined upper limit pixel number (step S206).

As described above, in the fake-finger determination device 1 according to the second embodiment, it is possible to classify the image captured by the imaging unit 10 into the skin region, the background region, and the remaining region. Then, if the number of pixels in the remaining region is equal to or greater than a predetermined number, it is possible to determine that a foreign substance is present in the periphery of the finger. As a result, even in the fake finger in which the transparent thin film is attached to the surface of the finger, it is possible to detect the thin film portion protruding in the periphery of the finger. Therefore, it is possible to improve determination accuracy of the fake finger.

In the fake-finger determination device 1 according to the second embodiment, it is determined whether or not the remaining region is the region obtained by excessively dividing the skin region or the background region. If it is determined that the remaining region is the excessively divided region, it is determined that the image corresponds to the human finger. As a result, it is possible to prevent a case where a finger of a genuine human is erroneously determined as a fake finger when the finger of the legitimate human is placed.

Embodiments described above are just exemplary and may encompass various modifications or technical applications although they are not specifically provided in the description of the embodiments. That is, the invention may be modified in various other forms without departing from the spirit or scope of the invention.

For example, although the image captured by the imaging unit 10 is classified into three regions including the skin region, the background region, and the remaining region according to the embodiments described above, the number of the classified regions is not limited to three. The image may be classified into a plurality of regions including at least the skin region and the background region.

Although it is assumed that the capturing range of the imaging unit 10 is larger than the authentication object, and a background is present in the periphery of the authentication object in the embodiments described above, such an assumption may not be satisfied. For example, if the capturing range of the imaging unit is small, the background or the film is not likely to appear in the captured image. If the background or the film does not appear in the captured image, it is impossible to identify the fake finger using the invention. Accordingly, it is preferable to use the present invention when the background appears in the captured image, and not to use the present invention when the background does not appear in the captured image. In order to implement such a configuration, for example, the following process may be further included in the fake-finger determination process described above.

If the ratio of a skin region with respect to the entire image captured by the imaging unit 10 is smaller than a predetermined value, the determining unit 32 determines that a background is present and then determines whether or not a foreign substance is present in the periphery of a finger. Meanwhile, if the ratio of the skin region with respect to the entire image captured by the imaging unit 10 is equal to or greater than the predetermined value, the determining unit 32 determines that a background is not present and skips the fake-finger determination process without determining whether or not a foreign substance is present in the periphery of a finger. The predetermined ratio may be set to, for example, a lower limit of the ratio when it is assumed that a background is not present. Through the process described above, the necessity of providing the imaging unit having a capturing range larger than the authentication object may be avoided.

Although the determining unit 32 according to the embodiments described above determines whether or not a foreign substance is present in the periphery of a finger based on the size of the remaining region, the criterion for determination is not limited to the size of the region. For example, it is possible to determine whether or not a foreign substance is present in the periphery of a finger based on such feature of the remaining region as a shape or position of the remaining region.

This application is based on and claims the priority of Japanese Patent Application No. 2009-256971 filed Nov. 10, 2009, hereby incorporated by reference as set forth fully herein.

While exemplary embodiments of the invention have been described and illustrated hereinbefore, they are not intended to limit the scope of the invention. They may be variously modified or changed without departing from the spirit or scope of the invention as appreciable by those skilled in the art.

The fake-finger determination device, the fake-finger determination method, and the fake-finger determination program according to the invention are suitably applied to determination of a fake finger in which a transparent thin film is attached to the finger surface.

1 fake-finger determination device
10 imaging unit
20 light source unit
30 control unit
31 classifying unit
32 determining unit

What is claimed is:

1. A device comprising:
a memory storing instructions; and
a processor executing the instructions to perform:
classifying the captured image into a skin region and a remaining region that is in periphery of a finger region and not treated as the skin region based on feature of pixels of the region included in the captured image; and
determining whether or not a foreign substance is present on the object based on the feature of the remaining region that is different from the finger region.

2. The device according to claim 1,
wherein the classifying the captured image into the skin region and the remaining region based on colors of pixels of the region included in the captured image.

3. The device according to claim 1,
wherein the determining whether or not the foreign substance is present on the object based on the size of the remaining region that is different from the finger region.

4. The device according to claim 1,
wherein the determining whether or not the foreign substance is present on the object based on the shape of the remaining region that is different from the finger region.

5. The device according to claim 1,
wherein the determining whether or not the foreign substance is present on the object based on the position of the remaining region that is different from the finger region.

6. The foreign substance determination device according to claim 1,
wherein the determining whether or not the remaining region is the region obtained by dividing the skin region.

7. The device according to claim 1,
wherein the classifying the captured image into the skin region, the remaining region and a background region.

* * * * *